United States Patent
Maassen et al.

(12)

(10) Patent No.: US 6,262,311 B1
(45) Date of Patent: Jul. 17, 2001

(54) PROCESS FOR THE PREPARATION OF 2,3, 5-TRIMETHYL-P-BENZOQUINONE

(75) Inventors: Ralf Maassen, Hanau; Steffen Krill, Speyer; Barbara Jäger, Freigericht; Klaus Huthmacher, Gelnhausen, all of (DE)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 09/688,185

(22) Filed: Oct. 16, 2000

(30) Foreign Application Priority Data

Oct. 15, 1999 (DE) ............................... 199 49 795

(51) Int. Cl.⁷ ..................... C07C 45/00; C07C 49/105
(52) U.S. Cl. ............................. 568/358; 362/377
(58) Field of Search ................ 552/310; 568/358, 568/362, 377

(56) References Cited

U.S. PATENT DOCUMENTS 5,041,572 * 8/1991 Jessel et al. ................... 552/310
5,104,996  4/1992 Hirose et al. .................. 552/310

FOREIGN PATENT DOCUMENTS

| 0 294 584 | 12/1988 | (EP) . |
| 475272 * | 3/1992 | (EP) . |
| 0 475 272 | 3/1992 | (EP) . |
| 54-98728 | 8/1979 | (JP) . |
| 5-97834 | 4/1993 | (JP) . |
| 9-202746 | 8/1997 | (JP) . |

* cited by examiner

*Primary Examiner*—Jose' G. Dees
*Assistant Examiner*—Alton Pryor
(74) *Attorney, Agent, or Firm*—Smith, Gambrell & Russell, LLP

(57) ABSTRACT

Process for the preparation of 2,3,5-trimethyl-p-benzoquinone by oxidizing 2,3,5-trimethylphenol or 2,3,6-trimethylphenol with oxygen or an oxygen-containing gas mixture in the presence of a catalyst system which can be a copper halide and a transition metal halide; for example iron, chromium, manganese, cobalt, nickel, zinc or a rare earth halide, in a two-phase reaction medium, at elevated temperature.

6 Claims, No Drawings

PROCESS FOR THE PREPARATION OF 2,3,5-TRIMETHYL-P-BENZOQUINONE

INTRODUCTION AND BACKGROUND

The present invention relates to a novel process for the preparation of 2,3,5-trimethyl-p-benzoquinone by oxidizing phenols by means of oxygen in the presence of a two-phase liquid reaction medium containing a catalyst mixture of copper chloride and additionally a transition metal halide selected from the group consisting of iron, chromium, manganese, cobalt, nickel, zinc and a halide of a rare earth element. Both 2,3,5-trimethylphenol and 2,3,6-trimethylphenol may be used as reactants in that process.

2,3,5-Trimethyl-p-benzoquinone is an intermediate which is used inter alia in the preparation of α-tocopherols (vitamin E).

The oxidation of trimethylphenols to 2,3,5-trimethyl-p-benzoquinone is known.

The use of inorganic oxidizing agents, including potassium permanganate, manganese dioxide and lead oxide, has been described, it being necessary in prior-known processes to use stoichiometric amounts of the oxidizing agent. The use of stoichiometric amounts of those expensive oxidizing agents causes high chemicals consumption and produces streams of waste which are polluted with the corresponding reduced metals and must be regenerated or disposed of at great expense.

Also known are catalytic processes in which the trimethylphenol oxidation is carried out in the presence of a metal catalyst using an oxygen-containing gas as the oxidizing agent. Conversion of those processes for commercial application, for example using a cobalt-salene complex catalyst, is complicated and expensive owing to the short life of the catalyst, since the addition of not inconsiderable amounts of fresh catalyst and the disposal or costly treatment of considerable amounts of discharge stream polluted with metals are necessary.

In EP 0 659 727, for example, tetraaza[14]annulene which contains a complex-bonded heavy metal ion is described as the oxygen-carrying catalyst. That catalyst complex is destroyed during the oxidation and is not recyclable, so that it is not suitable for commercial use.

In this connection, U.S. Pat. No. 3,796,732 describes the use of copper chloride as the catalyst for the reaction, wherein the operation is carried out in a homogeneous phase in the presence of an inert solvent such as DMF and there arises the problem of recovery of the catalyst, which can be solved technically only with a great expenditure.

In JP 17585/1978, an improvement in the yields is described using a catalyst system consisting of copper ions and halogen ions. Disadvantages of that process are that, in spite of good yields, the space-time yield is low and it is necessary to extract the catalyst using large amounts of water and to remove water in order to recycle the catalyst, and, not least, that residual water has a negative effect on the catalyst performance of the recycled catalyst.

In JP 93931/1975, halogens or halogenated compounds are added during the recycling in order to maintain the catalyst activity, but those compounds are used up rapidly under the reaction conditions and therefore must be supplemented regularly. That is expensive in terms of process technology and leads to markedly increased production costs.

A possible method of avoiding the problems of catalyst recycling while simultaneously maintaining catalyst activity is described in RU-2 039 037, in which the oxidation of trimethylphenol and structurally related compounds in the presence of a heterogeneous catalyst by means of oxygen or an oxygen-containing gas is disclosed.

A disadvantage of that process has proved to be the expensive preparation of the heterogeneous catalyst, which is obtained by applying a monovalent copper chloride in the presence of ammonium chloride and an alkali metal chloride to aluminum hydroxide as support in the presence of a defined amount of phosphoric acid.

According to EP 0 127 888, aqueous solutions of $Li(CuCl_3)$ in the presence of a high excess of the corresponding lithium halide are used as the oxidation catalyst. It has been found, however, that despite good yields, conversion of that process for commercial application is not advantageous because large excesses of expensive lithium halide must be used, the complex copper(II) catalyst must be expensively prepared before the reaction, and at least equivalent amounts of the catalyst, based on trimethylphenol, must be used to achieve good yields.

EP 0 167 153 describes the use of an aqueous catalyst solution consisting of $Li(CuCl_3)$ or corresponding copper(II) complexes in the presence of an excess of the corresponding lithium halide.

In EP 0 294 584 there is also described a process for the preparation of 2,3,5-trimethyl-p-benzoquinone in the presence of a catalyst consisting of copper(II) chloride and lithium chloride in a two-phase reaction medium consisting of water and a mixture of an aromatic hydrocarbon and a lower aliphatic alcohol having from 1 to 4 carbon atoms. The use of a complex organic solvent mixture, which must be recovered by distillation following the reaction, is not advantageous from a commercial point of view.

Another variant of the oxidation in a two-phase reaction system is described in EP 0 369 824. The catalyst consists of a binary system consisting of a copper(II) halide and a nitrogen-containing compound, preferably a hydroxylamine, an oxime or an amine or the corresponding ammonium salts. It has proved disadvantageous that the nitrogen-containing catalyst component is decomposed under oxidative conditions, cannot be recycled, and therefore gives rise to high costs.

EP 0 475 272 describes oxidation in the presence of an oxygen-containing gas using a catalyst consisting of a copper(II) halide and an alkaline earth metal halide in a two-phase solvent system consisting of water and a saturated aliphatic alcohol having from 5 to 10 carbon atoms. In that process, the active catalyst is formed in situ from the copper(II) salts and the alkaline earth metal additives and the organic solvent system has a sufficiently high flash point in comparison with the reaction temperatures used. However, in order to achieve good conversions and yields, the catalyst must be added in stoichiometric amounts.

The reaction in aliphatic alcohols having from 12 to 18 carbon atoms that is described in EP 0 387 820 likewise permits oxidation at temperatures below the flash point of the organic solvent, but the process is not very attractive commercially since the reaction and the isolation of the 2,3,5-trimethyl-p-benzoquinone are very complicated owing to the relatively high melting points and boiling points of the alcohols.

An object of the present invention is to provide a novel process for the preparation of 2,3,5-trimethyl-benzoquinone in order to solve the, in some cases, considerable disadvantages described in the prior art as regards the cost of the materials used, the outlay involved in working up and, not least, regarding safety aspects, which prevent conversion on a commercial scale.

More particularly, an object of the present invention is, especially, to meet the following requirements of the process:

a.) Use of a catalyst system consisting of inexpensive materials which are freely available on the market and which generate the active catalyst species in situ under the given reaction conditions, in contrast to the catalysts described hitherto, which in some cases must be prepared in separate process steps before the actual oxidation reaction or are used up during the reaction.

b.) Use of a catalyst system which is highly active and at the same time has a long life and which, after the reaction, can be recycled and used again repeatedly without special measures having to be taken.

c.) Use of a reaction system consisting of different phases which are immiscible at room temperature, one phase containing the catalyst in dissolved or suspended form and a further phase containing the substrate and product formed during the reaction in dissolved form, which allows the substrate/product phase on the one hand and the catalyst phase on the other hand to be separated after the reaction and accordingly enables the product to be isolated in a simple manner and in a high yield and allows the catalyst phase to be recycled at low cost.

SUMMARY OF THE INVENTION

The above and other objects of the invention can be achieved by converting trimethylphenol by oxidation with oxygen or an oxygen-containing gas mixture in the presence of a catalyst containing at least a copper halide in a two-phase reaction medium at elevated temperature.

A feature of the process is that the reaction is carried out in the reaction medium consisting of water and an aliphatic alcohol having from 5 to 10 carbon atoms or consisting of water and an aliphatic alcohol having from 1 to 4 carbon atoms and an aromatic hydrocarbon, in the presence of a catalyst system consisting of a copper halide and additionally a transition metal halide selected from the group consisting of iron, chromium, manganese, cobalt, nickel, zinc and a halide of a rare earth element, at temperatures of from 20 to 120° C.

The reaction may be so carried out that the organic phase containing the trimethylphenol substrate and consisting of a suitable solvent that is not or only slightly water-soluble at room temperature is brought into contact with the aqueous phase containing the catalyst system, and the reaction mixture so prepared is brought into contact with an oxygen-containing gas and, when the reaction is complete, the organic product phase is separated from the aqueous, still active catalyst phase in order to isolate the 2,3,5-trimethyl-p-benzoquinone product.

That result was unexpected because, in aqueous systems of copper halides and transition metal halides or halides of rare earth elements, the formation of sparingly soluble, in some cases oligomeric or polymeric hydrolysis products, which exhibit no selective catalytic action for the studied oxidation, must be reckoned with.

DETAILED DESCRIPTION OF INVENITON

It has been found in the case of the present invention that, if a binary catalyst system consisting of copper halides on the one hand and transition metal halides or halides of elements from the group of the rare earths on the other hand is used, no or only negligible deactivation of the catalyst occurs, even when the aqueous catalyst phase is used repeatedly, and the oxidation to 2,3,5-trimethyl-p-benzoquinone may be carried out under the novel conditions in a manner that is both economical and advantageous from a commercial point of view.

Yields of 2,3,5-trimethyl-p-benzoquinone of over 90% can be achieved even when the catalyst phase is used repeatedly. The use of selected transition metal halides, such as, for example, $CrCl_3$, $FeCl_3$ or $ZnCl_2$, offers a further economical advantage as compared, for example, with the use of expensive LiCl.

The oxidizing agent used in the process according to the invention is oxygen in pure form or in dilute form, for example air. Based on 1 liter of reaction mixture, from 10 to 150 NL of gaseous oxygen are generally supplied per hour. There may be mentioned as copper salts that are suitable within the scope of the invention, without laying any claim to completeness, substantially $CuCl_2$ and $CuBr_2$ or corresponding Cu(I) salts such as CuCl or CuBr, especially $CuCl_2$ and CuCl. Preference is given to the use of Cu(II) chloride.

There may be mentioned as transition metal halides that are suitable within the scope of the invention substantially chlorides of the transition metals. Especially suitable are the halides of the elements of the fourth period, such as, for example, halides of the elements Cr, Mn, Fe, Co, Ni and Zn, as well as Ce from the group of the rare earths.

There are suitable as the reaction medium in admixture with water especially branched and unbranched aliphatic $C_5$–$C_{10}$, alcohols, such as 1-pentanol, 1-hexanol, 1-heptanol, 1-octanol, 1-nonanol, 1-decanol, 2-ethylhexanol or cyclohexanol.

Also suitable as the reaction medium in admixture with water and an aromatic hydrocarbon are branched and unbranched aliphatic alcohols, such as methanol, ethanol, n-propanol, isopropanol, 1-butanol, 2-butanol and tert.-butanol.

The aromatic hydrocarbons used are preferably those having from 6 to 8 carbon atoms, especially benzene, toluene, xylenes, or halo-substituted aromatic compounds, such as chlorobenzene.

The aqueous catalyst phase is prepared by simply mixing the aqueous solutions of the individual components or by dissolving the solid salt compounds in water, which makes the process markedly simpler to carry out.

The molar ratio of copper halide to trimethylphenol may be varied within wide ranges and is usually copper salt/trimethylphenol=from 0.1 to 10, preferably from 0.2 to 3.

The transition metal halides may be used in a 0.1- to 10-fold amount, based on trimethylphenol, preference is given to a 0.2- to 5-fold molar amount. In the case of the use of copper(II) salts, the concentration of the copper halide in the aqueous catalyst phase may be varied from 1 to 70 wt. %, concentrations of from 5 to 30 wt. % are preferably used, the transition metal halides or the rare earth halides are preferably used in a concentration range of from 5 to 80 wt. %.

There may be used as additional activators for the reactions the systems known from the prior art, copper salts such as copper(I) chloride or the corresponding hydroxide are most advantageously used.

Two-phase mixtures which result, for example, from the use of water and a solvent that is immiscible or miscible to only a limited extent with water, are optionally provided with a phase-transfer catalyst. There come into consideration as phase-transfer catalysts the conventional products known per se, such as tetraalkylammonium halides, benzyltrialkylammonium halides or hydrogen sulfates as well as the corresponding phosphonium salts and also compounds from the group of the polyethylene glycols. The novel process is generally carried out at normal pressure and at a temperature of from 20 to 120° C. The process may likewise be carried out under pressure; operation under pressure is appropriate especially in the case of oxygen-containing gas mixtures. The procedure may be carried out both continuously and discontinuously.

In order to carry out the reaction, trimethylphenol is dissolved in the organic component of the solvent system and added in metered amounts to the aqueous phase containing the catalyst. In a different embodiment, a portion of the organic solvent is placed in a vessel with the aqueous phase before the start of the reaction, and the trimethylphenol solution is added in metered amounts. In yet another variant of the reaction procedure, the reaction is carried out batchwise, all the components being placed in a vessel, with stirring, and the metered addition of the oxygen-containing gas then being begun.

The concentration of trimethylphenol in the organic phase may be varied within wide concentration ranges, the trimethyl-phenol concentration is generally adjusted to from 5 to 80%, preferably from 10 to 50%.

The ratio by volume of water to organic solvent may vary within a range of from 10:1 to 1:10, a range of from 3:1 to 1:5 is preferred.

The reaction temperature may be varied over a wide temperature interval, the reaction is preferably carried out at from 20 to 1200° C., in an especially preferred embodiment the procedure is carried out at from 40 to 900° C.

Sciences Inc. The above-described TMQ reference substance was used as the external standard.

The Examples which follow are intended to explain the invention in greater detail.

TMP stands for trimethylphenol.

TMQ stands for 2,3,5-trimethyl-p-benzoquinone.

EXAMPLES

Example 1

2.98 g of $FeCl_3$ (18.4 mmol) and 0.91 g (9.2 mmol) of CuCl were dissolved in water in a 100 ml three-necked flask (molar ratio $CuCl:FeCl_3=0.5$). The catalyst concentration of the binary salt mixture was 13.5 wt. % in the aqueous phase. A solution of 2.5 g of TMP (=18.4 mmol) in 25 ml of hexanol was added to the aqueous catalyst phase with vigorous stirring. The TMP concentration in the organic phase was 11 wt. %. The reaction mixture was heated to 60° C., while gassing with oxygen over a frit, and the progress of the reaction was monitored by means of gas chromatography. When the reaction was complete, a TMQ yield of 82.2% was obtained.

Examples 2 to 6

Analogously to Example 1, the components were placed in a 100 ml three-necked flask, the $TMP:CuCl_2:FeCl_3$ ratio being 1:0.75:1.5. The concentration of the binary catalyst in the aqueous phase was 39.4 wt. % in all the tests. The TMP-alcohol solution was added to the catalyst phase used initially, the mixture was then brought to the indicated temperature, and gassing with oxygen was begun. By varying the reaction temperatures and the reaction times, the following results were obtained at the end of the reaction.

TABLE 1

| Example | Alcohol | Catalyst (molar amount) | Stoichiometry $TMP/CuCl_2/FeCl_3$ | Temp. (° C.) | $H_2O$/solvent wt./wt. | TMP conc. in the solvent (wt. %) | Time (h) | TMQ yield (GC % by surface area) |
| --- | --- | --- | --- | --- | --- | --- | --- | --- |
| 2 | 1-hexanol | $CUCl_2$ (0.066) $FeCl_3$ (0.132) | 1:0.75:1.5 | 70 | 1:0.79 | 24.6 | 1 | 97.7 |
| 3 | 1-octanol | $CuCl_2$ (0.066) $FeCl_3$ (0.132) | 1:0.75:1.5 | 70 | 1:0.80 | 24.2 | 1 | 87.8 |
| 4 | 1-hexanol | $CuCl_2$ (0.066) $FeCl_3$ (0.132) | 1:0.75:1.5 | 40 | I:0.79 | 24.6 | 4 | 91.2 |
| 5 | 1-hexanol | $CUCl_2$ (0.066) $FeCl_3$ (0.132) | 1:0.75:1.5 | 60 | 1:0.79 | 24.6 | 2 | 93.4 |
| 6 | 1-hexanol | $CuCl_2$ (0.066) $FeCl_3$ (0.132) | 1:0.75:1.5 | 80 | 1:0.79 | 24.6 | 1 | 93.9 |

The 2,3,5-trimethyl-p-benzoquinone reaction product may be isolated in the conventional manner, for example by means of vacuum and steam distillation.

The process according to the invention is simple to carry out and supplies the reaction product in a good yield and a high purity.

The yields were determined on a HP 5890 or HP 6890 gas chromatograph using a J&W DB-5 capillary column having a length of 30 m, an inside diameter of 0.32 mm and a film thickness of 1 μm. Tetradecane was used as the internal standard. The reference substance used was TMQ, which was purified by distillation and repeated crystallisation.

HPLC measurements were carried out on a system from Jasco, consisting of a UV 975 UV detector, a PU 980 pump and an AS 950 automatic sampler. The column used was an Intersil-ODS 3V-5μ250×4.6 mm inside diameter from GL Examples 7 to 12

Copper(II) chloride and a transition metal chloride or a chloride of a rare earth element were placed in the form of an aqueous solution in a glass reactor in the amounts indicated in Table 2; 40 ml of 1-hexanol were added and the mixture was heated to 65° C. A solution of 12 g of 2,3,6-trimethylphenol (88 mmol) in 20 ml of 1-hexanol was then added dropwise in the course of 3 hours, with stirring (900 rpm) and while gassing with oxygen over a frit. When the addition was complete, stirring was continued for a further 2 hours at 80° C., while gassing with oxygen, and the progress of the reaction was monitored by HPLC. When the reaction was complete, the phases were separated, the organic phase was washed twice with water, and the TMQ yield was determined by gas chromatography using an internal standard.

TABLE 2

| | Catalyst (molar amount [mmol]) | Catalyst conc. in the aqueous phase (wt. %) | Stoichiometry TMP/CuCl$_2$/add. | H$_2$O/solvent wt./wt. | TMQ yield (%) |
|---|---|---|---|---|---|
| Example 7 | CuCl$_2$ (0.066) CrCl$_3$ (0.132) | 39.0 | 1:0.75:1.5 | 1:1.05 | 94.3 |
| Example 8 | CuCl$_2$ (0.066) MnCl$_2$ (0.132) | 40.9 | 1:0.75:1.5 | 1:1.33 | 93.7 |
| Example 9 | CuCl$_2$ (0.066) CoCl$_2$ (0.132) | 35.8 | 1:0.75:1.5 | 1:1.05 | 91.1 |
| Example 10 | CuCl$_2$ (0.066) NiCl$_2$ (0.132) | 38.4 | 1:0.75:1.5 | 1:1.18 | 93.0 |
| Example 11 | CuCl$_2$ (0.066) ZnCl$_2$ (0.066) | 50.7 | 1:0.75:0.75 | 1:2.82 | 89.9 |
| Example 12 | CuCl$_2$ (0.066) CeCl$_3$ (0.132) | 45.8 | 1:0.75:1.5 | 1:1.00 | 91.5 |

Example 13

Copper(II) chloride (66 mmol) and chromium(III) chloride (132 mmol) were placed in the form of an aqueous solution in a glass reactor (catalyst concentration in the aqueous phase: 39.0 wt. %); 40 ml of 1-hexanol were added and the mixture was heated to 65° C. A solution of 12 g of 2,3,6-trimethylphenol (88 mmol) in 20 ml of 1-hexanol was then added dropwise in the course of 3 hours, with stirring (900 rpm) and while gassing with oxygen over a frit. When the addition was complete, stirring was continued for a further 2 hours at 80° C., while gassing with oxygen, and the progress of the reaction was monitored by HPLC. When the reaction was complete, the phases were separated, the organic phase was washed twice with water, and the TMQ yield was determined by gas chromatography using an internal standard. The combined aqueous phases were concentrated to the original volume in a rotary evaporator and transferred to the glass reactor again as the catalyst solution. The process was repeated several times.

TABLE 3

| Example 13, run | Number of repetitions of the process | TMQ yield (%) |
|---|---|---|
| 1 | 1 | 92.0 |
| 2 | 2 | 94.2 |
| 3 | 3 | 94.3 |
| 4 | 4 | 93.8* |
| 5 | 5 | 93.7 |
| 6 | 6 | 92.3 |
| 7 | 7 | 94.3 |

*HPLC analysis using an external standard

Examples 14 to 17

Copper(II) chloride (66 mmol) and chromium(III) chloride (132 mmol) were placed in the form of an aqueous solution in a glass reactor (catalyst concentration in the aqueous phase: 39.0 wt. %); the amount of the respective alcohol indicated in Table 4 was added, and the mixture was heated to the indicated temperature. A solution of 12 g of 2,3,6-trimethylphenol (88 mmol) in the amount of the respective alcohol shown in Table 4 was then added dropwise in the course of 3 hours, with stirring (900 rpm) and while gassing with oxygen over a frit. When the addition was complete, stirring was continued for the time shown in Table 4 at the indicated temperature, while gassing with oxygen, and the progress of the reaction was monitored by HPLC. When the reaction was complete, the phases were separated, the organic phase was washed twice with water, and the TMQ yield was determined by HPLC using an external standard.

Further variations and modifications will be apparent to those skilled in the art from the foregoing and are intended to be encompassed by the claims appended hereto.

German priority application 199 49795.8 is relied on and incorporated herein by reference.

TABLE 4

| | Alcohol | Amount of alcohol used initially (ml) | Amount of alcohol for the TMP solution (ml) | Temperature during the dropwise addition (° C.) | Temperature during subsequent stirring (° C.) | Subsequent stirring time (h) | TMQ yield (%) |
|---|---|---|---|---|---|---|---|
| Example 14 | 1-heptanol | 40 | 20 | 65 | 80 | 2 | 93.6 |
| Example 15 | 1-heptanol | 40 | 20 | 70 | 70 | 5 | 93.3 |
| Example 16 | 1-octanol | 30 | 30 | 65 | 80 | 2 | 92.7 |
| Example 17 | 1-octanol | 30 | 30 | 75 | 75 | 4 | 94.7 |

What is claimed is:

1. A process for the preparation of 2,3,5-trimethyl-p-benzoquinone comprising oxidizing trimethylphenol with oxygen or an oxygen-containing gas mixture in the presence of a catalyst in a two-phase reaction medium at a temperature of 20 to 120° C., wherein the reaction medium consists of water and an aliphatic alcohol having from 5 to 10 carbon atoms or consists of water and an aliphatic alcohol having from 1 to 4 carbon atoms and an aromatic hydrocarbon, and wherein the catalyst comprises a copper halide and additionally a transition metal halide selected from the group consisting of iron, chromium, manganese, cobalt, nickel, zinc and a halide of a rare earth element.

2. The process for the preparation of 2,3,5-trimethyl-p-benzoquinone according to claim 1, wherein said reaction medium is water and a mixture of an aliphatic alcohol having from 1 to 4 carbon atoms and toluene or benzene.

3. The process for the preparation of 2,3,5-trimethyl-p-benzoquinone according to claim 1, wherein said reaction medium is water and 1-hexanol, 1-heptanol, 2-ethylhexanol or 1-octanol.

4. The process for the preparation of 2,3,5-trimethyl-p-benzoquinone according to claim 1, wherein chromium(III), manganese(II) or cobalt(II) chloride is the transition metal halide.

5. The process for the preparation of 2,3,5-trimethyl-p-benzoquinone according to claim 1, wherein cerium(III) chloride is the halide of a rare earth element.

6. The process for the preparation of 2,3,5-trimethyl-p-benzoquinone according to claim 1 further comprising bring an organic phase containing said trimethylphenol into contact with an aqueous phase containing said catalyst to produce a reaction mixture, bring said reaction mixture into contact with said oxygen-containing gas mixture, and after completion of a reaction to produce said benzoquinone, separating the organic phase from the acqueous phase.

* * * * *